United States Patent
Marsh et al.

[11] Patent Number: 5,931,837
[45] Date of Patent: Aug. 3, 1999

[54] METHOD AND APPARATUS FOR EXTERNAL FIXATION OF AN ANKLE

[75] Inventors: J. Lawrence Marsh; Michael Bottlang, both of Iowa City, Iowa

[73] Assignee: University of Iowa Research Foundation, Iowa City, Iowa

[21] Appl. No.: 08/987,511

[22] Filed: Dec. 9, 1997

[51] Int. Cl.⁶ .................................................. H61B 17/60
[52] U.S. Cl. .............................................. 606/55; 606/54
[58] Field of Search ................................ 606/55, 54, 56, 606/57, 58, 59, 73

[56] References Cited

U.S. PATENT DOCUMENTS

| | | | |
|---|---|---|---|
| 2,020,262 | 11/1935 | Longfellow | 128/44 |
| 5,112,140 | 5/1992 | Asche et al. | 606/55 |
| 5,437,667 | 8/1995 | Papierski et al. | 606/55 |
| 5,620,442 | 4/1997 | Bailey et al. | 606/54 |
| 5,662,650 | 9/1997 | Bailey et al. | 606/59 |

OTHER PUBLICATIONS

Bonar, S.K., Marsh, J.L.; Unilateral External Fixation For Severe Pilon Fractures, Foot and Ankle, 14:57–64, 1993.

Marsh, J.L., Bonar S., Nepola, J.V., DeCoster, T.A., Hurwitz, S.R., Use of An Articulated External Fixator For Fractures of the Tibial Plafond; J Bone Joint Surg 77–A:1498–1509, 1995.

Fitzpatrick, D.C., Marsh, J.L., and Brown T.D.; Articulated External Fixation of Pilon Fractures: The Effects On Ankle Joint Kinematics; J. Orthop Trauma; 9:76–82, 1995.

Fitzpatrick, D.; Foels, W.S., Pedersen, D.R.; Marsh, J.L; Saltzman, C.L., Brown, T.D.; An Articulated Ankle External Fixation System That Can Be Aligned With the Ankle Axis; Iowa Orthop. Journal, vol. 15, 197–203, 1995.

Bottlang, M., Marsh, J.L., Brown, T.D.; Pathway of Instant Axes of Rotation of the Ankle Joint for the Application of External Articulated Fixation. Abstract, 2 pages, undated.

Bottlang, M., Marsh, J.L., Brown, T.D.; Articulated External Ankle Fixation: Effect of Hinge Axis Position on Joint Kinetics, 2 pages, undated.

EBI Medical Systems brochure, "New Ball Joint Articulating Ankle", 1 page, dated Jul., 1994.

EBI Medical Systems brochure, "If You Think Orthofix Is Just for Fractures . . . Think Again!", 1 page, dated Jan., 1994.

*Primary Examiner*—Guy V. Tucker
*Attorney, Agent, or Firm*—Harness, Dickey & Pierce, P.L.C.

[57] ABSTRACT

A fixator for adjustably securing a first skeletal element on a superior side of an ankle joint relative to a skeletal element on the inferior side of the ankle joint. The fixator includes a bone screw clamping assembly that preferably secures a pair of screws to the bones of the foot. The bone screw clamping assembly is attached to a central body of the fixator and is operative for articulating the pair of bone screws about an axis substantially co-axial with the anatomical pivot axis of the ankle joint. The bone screw clamping assembly further defines a radiographic window for permitting lateral radiographic examination of the anatomical pivot axis of the ankle joint.

17 Claims, 4 Drawing Sheets

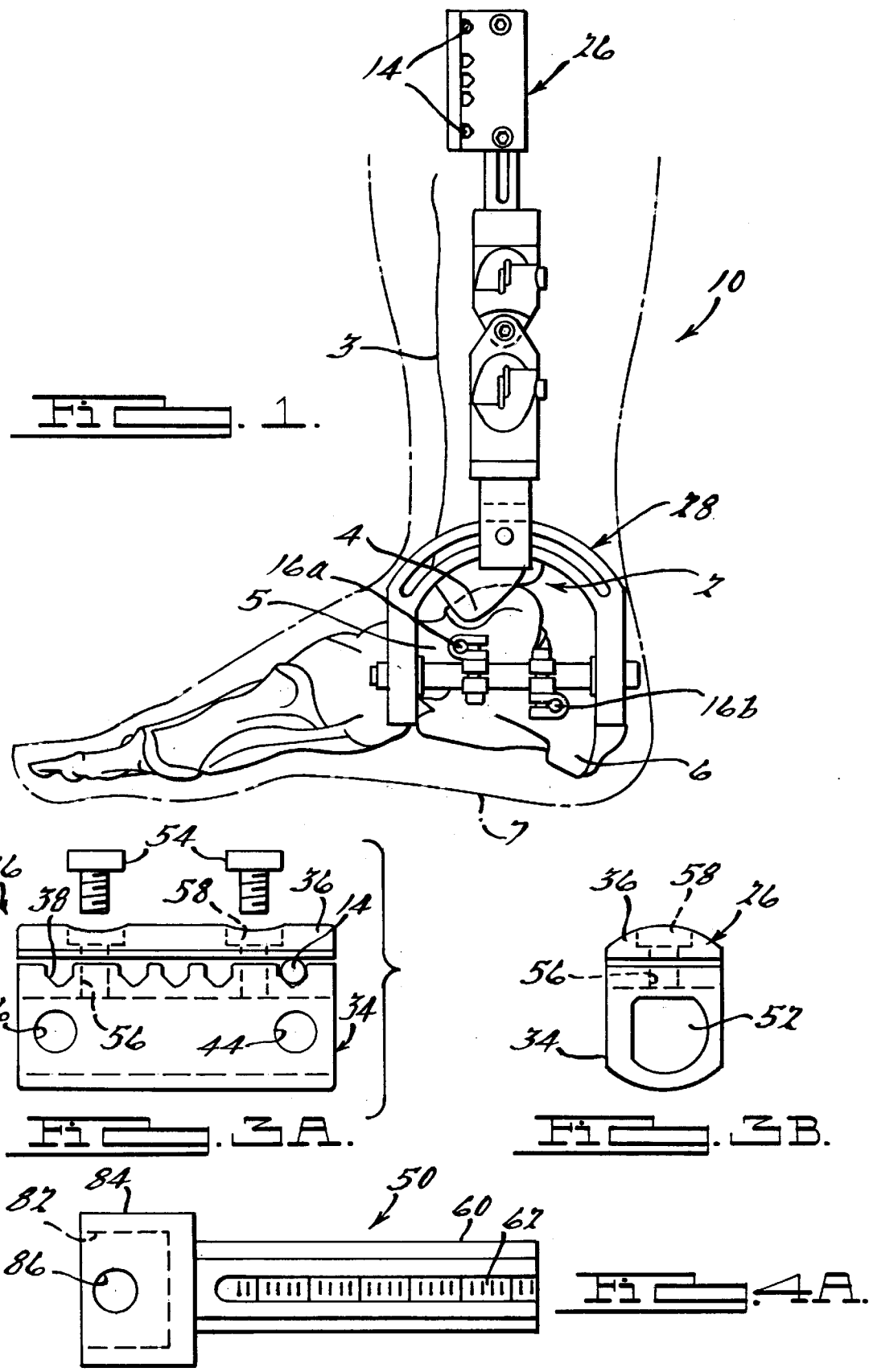

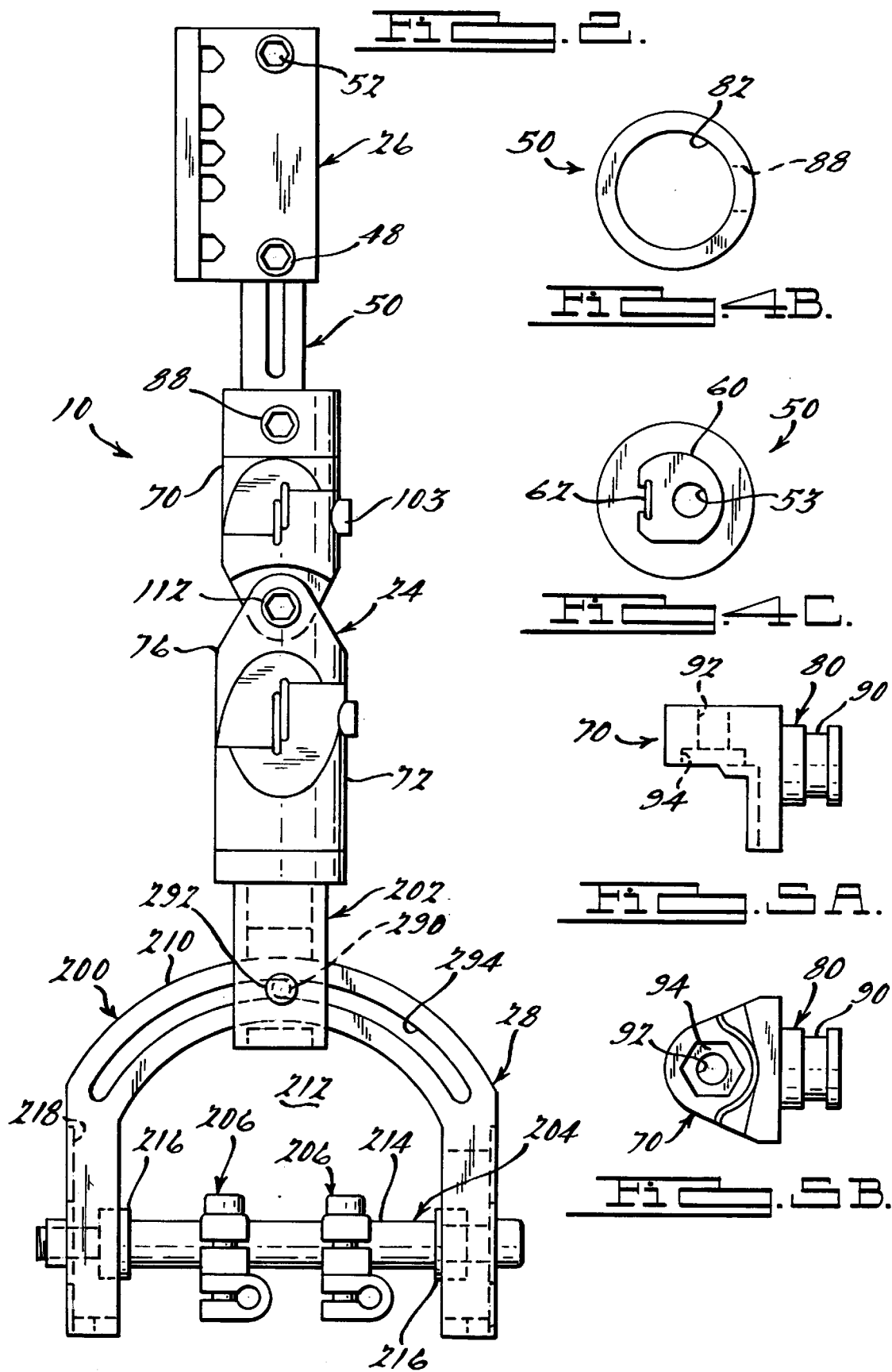

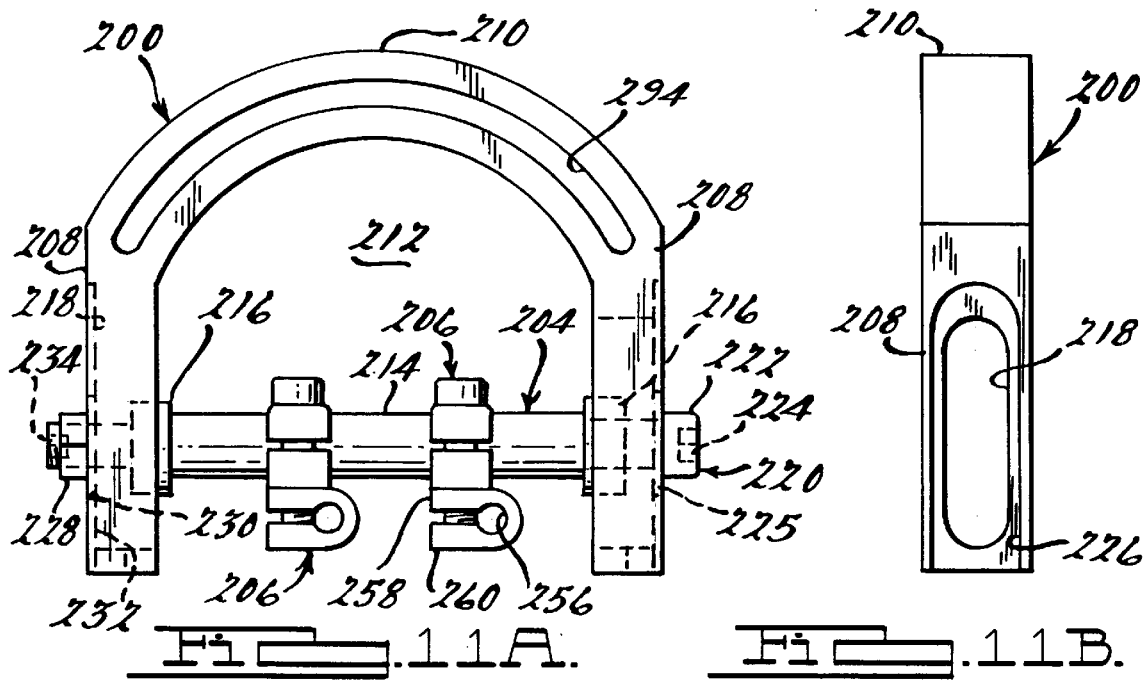
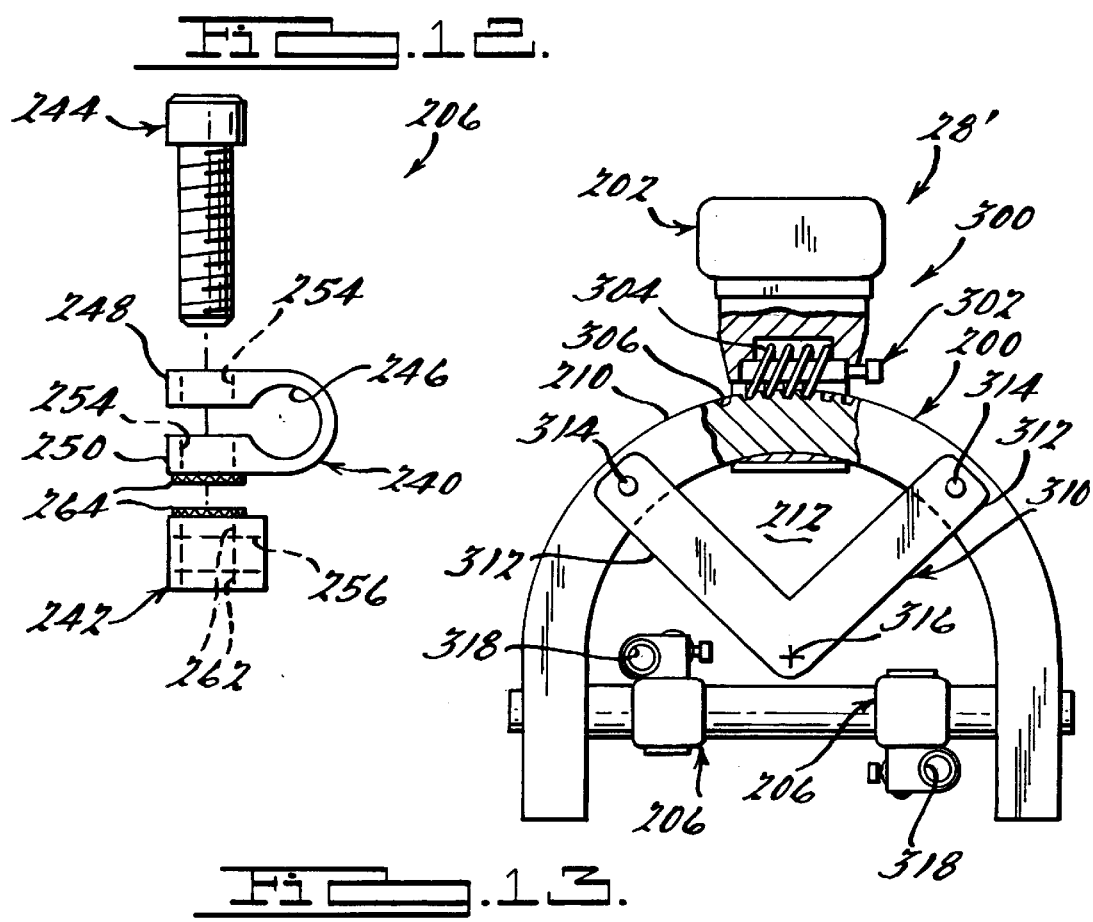

METHOD AND APPARATUS FOR EXTERNAL FIXATION OF AN ANKLE

BACKGROUND OF THE INVENTION

1. Field of the Invention

The present invention relates to an external fixator for use in orthopedic surgical applications, and more particularly to a method and apparatus for external fixation of an ankle.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed and in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to employ an external fixation device for immobilizing or restricting motion of the ankle joint. One known external fixator for an ankle joint is a monolateral cross-ankle articulated fixator manufactured by Orthofix SRL. This fixator is intended to allow motion at the ankle joint as a fracture heals. The fixator is applied with two pins distally, one in the talus and one in the calcaneus, and two pins proximally in the tibia. A distal clamp is attached to a body of the fixator by a uniaxial hinge that is centered over the medial side of the talus. The hinge axis is aligned along the horizontal ankle axis. The hinge is released post-operatively so that the patient may perform passive and active motion.

While known external fixators specifically designed for supporting an ankle joint may have proven to be acceptable for certain applications, such fixators are nevertheless susceptible to improvements that may enhance their performance. In this regard, the hinge position for known external fixators is established by insertion of talar and calcanear pins, thereby requiring pin positioning to accommodate hinge adjustment. Additionally, the clamps of known ankle fixators force the calcanear and talar pins to be parallel. This is true even if the calcanear and talar pins are not inserted exactly parallel. Furthermore, radiographic examination of the ankle joint is typically hindered by conventional ankle fixators since the anatomical pivot axis of the human ankle joint is aligned with structure defining a pivot axis of the fixator.

SUMMARY OF THE PRESENT INVENTION

In general, the present invention relates to an external fixator for use as an orthopedic device for stabilizing a hinged joint. More specifically, the present invention relates to an external fixator which is operable to adjustably secure a skeletal element located on a proximal side of an ankle joint in a particular position with respect to a skeletal element on the distal side of the ankle joint. The external fixator includes a first means for receiving a bone screw which is preferably secured to the tibia. In addition, the external fixator includes a second means for receiving a second bone screw which is preferably secured to the foot. The means for receiving the second bone screw defines a radiographic window for permitting radiographic examination of the anatomical pivot axis of the ankle joint. The means for receiving the second bone screw includes first and second hinge components which cooperate to pivot the second bone screw about an axis substantially coaxial with the anatomical pivot axis. The external fixator also includes a main body which is operable to connect the first means for receiving the first bone screw with a second means for receiving the second bone screw. Once the second bone screw is attached to the first, the means for receiving the second bone screw can be adjusted to receive the second bone screw for pivotal attachment about the anatomical pivot axis.

An advantage of the present invention is the provision of a method and apparatus for external ankle fixation which allows for optimal alignment through hinge positioning which is independent from bone pin placement.

A related advantage of the present invention is the provision of a method and apparatus for external fixation which affords flexible pin placement to avoid damage to local neurovascular structures and ligaments.

Another advantage of the present invention is the provision of a method and apparatus for external ankle fixation which permits movement of a hinge assembly relative to bone pins engaged with the bones of the foot.

Another advantage of the present invention is the provision of a method and apparatus for external ankle fixation which allows complete radiographic access of the ankle joint from the lateral view to determine "best fit" hinge axis.

Another advantage of the present invention is the provision of a method and apparatus for external ankle fixation which facilitates symmetric ankle joint distraction.

Another advantage of the present invention is the provision of a method and apparatus for external ankle fixation which permits a controlled range of motion.

Another advantage of the present invention is the provision of a method and apparatus for external fixation of an ankle joint which permit rotation of bone screws with associated bone screw clamps to substantially eliminate torque at the bone/screw interface.

Additional advantages and features of the present invention will become apparent from the following description and appended claims, taken in conjunction with the accompanying drawings.

BRIEF DESCRIPTION OF THE DRAWINGS

FIG. 1 is an elevational view of the apparatus for external fixation of an ankle joint according to the teachings of the preferred embodiment of the present invention shown in operative association with a human ankle joint.

FIG. 2 is an enlarged elevational view of the apparatus for external fixation of an ankle joint according to the teachings of the preferred embodiment of the present invention.

FIGS. 3(A)–(B) are illustrations showing the central body of the bone screw clamping assembly shown in FIG. 2 according to the teaching of the preferred embodiment of the present invention.

FIGS. 4(A)–(C) are illustrations of a rail member shown in FIG. 2 according to the teachings of the preferred embodiment of the present invention.

FIGS. 5(A)–(B) are illustrations of a first connector member shown in FIG. 2 according to the teachings of the preferred embodiment of the present invention.

Figure 6:
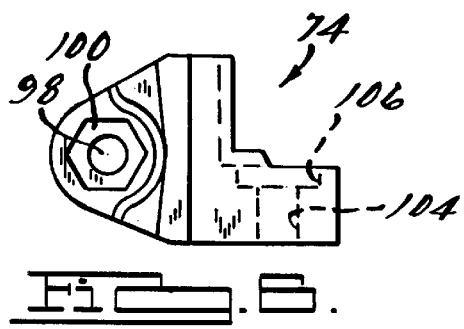

FIG. 6 is an illustration of a first rotational component shown in FIG. 2 according to the teachings of the preferred embodiment of the present invention.

Figure 7:
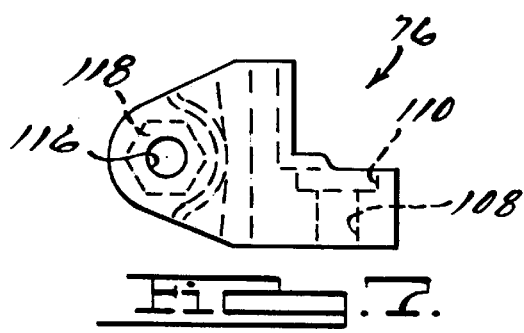

FIG. 7 is an illustration of a second rotational component shown in FIG. 2 according to the teachings of the preferred embodiment of the present invention.

Figure 8A:
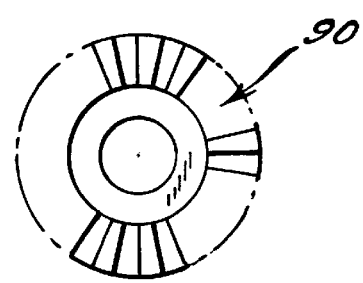
Figure 8B:
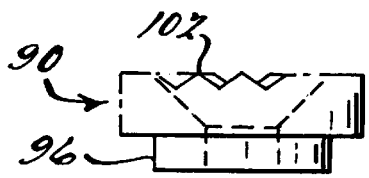

FIGS. 8(A)–(B) are illustrations showing one of the grooved locking washers shown in FIG. 2 according to the teachings of the preferred embodiment of the present invention.

Figure 9A:
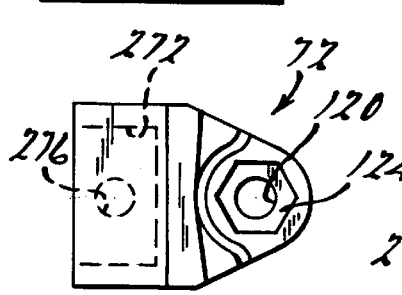
Figure 9B:
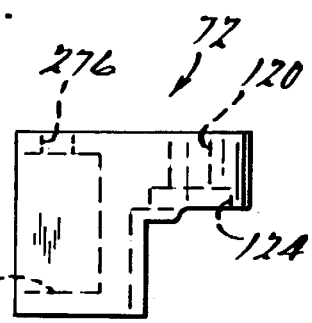
Figure 9C:
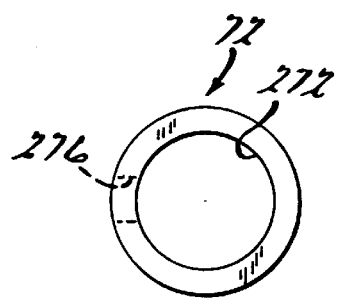

FIGS. 9(A)–(C) are illustrations of a second connection member shown in FIG. 2 according to the teachings of the preferred embodiment of the present invention.

Figure 10A:
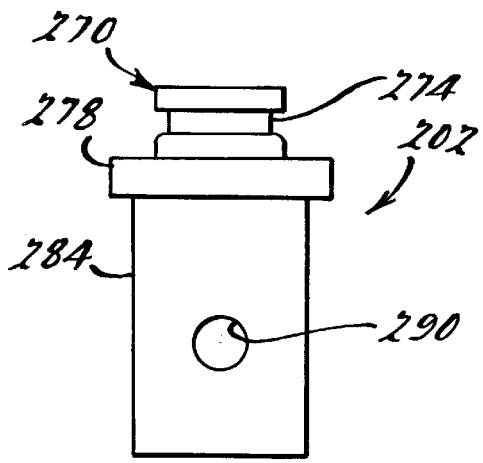
Figure 10B:
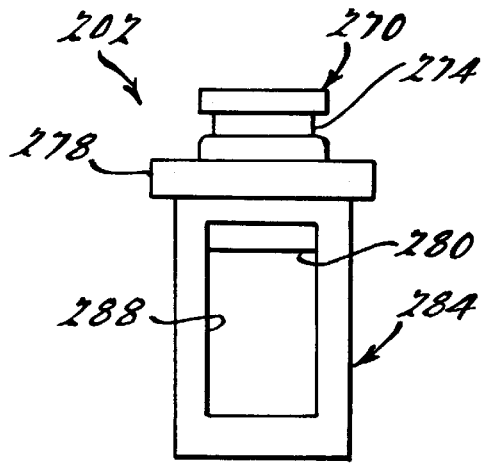

FIGS. 10(A)–(B) are illustrations of the second hinge component shown in FIG. 2 according to the teachings of the preferred embodiment of the present invention.

FIGS. 11(A)–(B) are illustrations of the first hinge component shown in FIG. 2 according to the teachings of the preferred embodiment of the present invention.

FIG. 12 is an exploded view of one of the bar clamps shown in FIG. 11A according to the teachings of the preferred embodiment of the present invention.

FIG. 13 is an elevational view of a portion of an apparatus for external fixation of an ankle joint according to the teachings of the alternative embodiment of the present invention.

DETAILED DESCRIPTION OF THE PRESENT INVENTION

The following description of the preferred embodiment of the present invention is merely exemplary in nature and is in no way intended to limit the invention or its application or uses.

Referring to FIG. 1, an apparatus for external fixation is shown operatively associated with a human ankle joint or talocrural joint is generally identified with reference numeral 10. Before addressing the construction and function of the apparatus 10, a brief understanding of the pertinent anatomy shown in FIG. 1 is warranted. In this regard, an ankle joint 2 is principally uniaxial and classified as a hinge joint. The structures entering into its formation above include the lower end of the tibia 3 which cooperates with the fibula (not specifically shown) to form a deep cavity for the reception of the proximal convex surface of the talus 5 and its medial and lateral facets. The calcaneus 6 is the largest and strongest bone in a human foot 7. It is situated in the posterior part of the foot 7 and extends backward beyond the tibia 3 and fibula to form the heel. The calcaneus 6 serves to transmit the weight of the body to the ground and provides a strong lever for the muscles of the calf.

With continued reference to FIG. 1, the apparatus 10 is shown connected to a first skeletal element on the proximal side of the ankle joint 2 and second and third skeletal elements on the distal side of the ankle joint 2. Preferably, the apparatus 10 is connected on the proximal side to the tibia 3 through at least one bone screw 14 and on the distal side to the bones of the foot 7 through a pair of bone screw 16. In the preferred embodiment, a first bone screw 16a secures the apparatus 10 to the talus 5 and a second bone screw 16b secures the apparatus 10 to the calcaneus 6. By securing the tibia 3, talus 5 and calcaneus 6 in this manner, the anatomical pivot access of the ankle joint 2, which is located therebetween, may be stabilized. While the apparatus 10 is specifically shown associated with an ankle joint 2, it is to be understood that the teachings of the present invention may be adapted for use with other hinged joints of the body.

The apparatus 10 is shown to generally comprise a central body 24 as well as a first bone screw clamping assembly 26 and a second bone screw clamping assembly 28. The central body 24 is articulated to allow the apparatus 10 to axially rotate so as to provide a proper longitudinal rotational location of the bone screws 14 and 16 with respect to their associated bone(s) 3, 5 and 6. The first bone screw clamping assembly 26 is used to secure the bone screw 14 to the apparatus 10 while permitting the bone screw 14 to be axially displaced from the central body 24. The second bone screw clamping assembly 28 is able to secure bone screws 16a and 16b to the apparatus 10.

The principal focus of the present invention relates to the construction and operation of the second clamping assembly 28. In this regard, it will be understood that the central body 24 and the first bone screw clamping assembly 26 may be of any suitable configuration for interconnecting the tibia 3 with the second bone screw clamping assembly 28. For purposes of fully describing the exemplary embodiment illustrated throughout the drawings, the second clamping assembly 28, as well as the first bone screw clamping assembly 26 and the central body 24, will be more fully discussed below.

The first bone screw clamping assembly 26 will be described in greater detail with reference to FIGS. 3(A)–3 (B). The first bone screw clamping assembly 26 includes a base portion 34 and a cover portion 36. The base portion 34 preferably serves to receive two bone screws 14 in two of a plurality of grooves 38, while the cover portion 36 serves to secure the bone screws 14 within the grooves 38. The grooves 38 include two contact surfaces which are substantially planar so as to permit line contact of the bone screws 14 in two positions within the grooves 38. Since the first bone screw 14 also engages the cover portion 36 of the first bone screw clamping assembly 26, the bone screws 14 engage the first bone screw clamping assembly 26 in three positions (i.e., along the contact surfaces as well as on the cover portion 36). This provides line contact for the bone screw 14 which secures the bone screws 14 in a more effective manner than if the grooves 38 were cylindrical.

The base portion 34 of the bone screw clamping assembly 26 further includes a first aperture 44 and a second aperture 46. The first aperture 44 is used to receive a threaded member 48 which serves to secure a rail member 50 in a locked position as will be more fully discussed below. The second aperture 46 is used to receive a threaded member 52 which is able to secure a compression/distraction member (not shown) within a D-shaped central bore 52 of the bone screw clamping assembly 26. One suitable compression/distraction member is shown and described in U.S. Pat. No. 5,662,650. The compression/distraction member engages a threaded aperture 53 located in the D-shaped extension 60.

The cover portion 36 of the first bone screw clamping 26 is secured to the base portion 34 of the first bone screw clamp 30 by means of two screws 54. To accommodate these screws 54, the cover portion 36 of the bone screw clamping assembly 26 includes two apertures 56 (shown in phantom in FIGS. 3(A) and 3(B)) which mate with corresponding apertures 58 in the base portion 34 of the bone screw clamp 26. Accordingly, upon secured threaded engagement of the screws 54 within the apertures 56 and 58, the cover portion 36 of the bone screw clamp 36 may be secured to the base portion 34 of the bone screw clamp 26.

To provide means for laterally displacing the first bone screw clamp 26 with respect to the central body 24, the bone screw clamping assembly 26 further includes a rail member 50. The rail member 50, which is illustrated most clearly in FIGS. 4A–4C, includes a D-shaped extension 60 which is able to receive in the D-shaped bore 52 of the bone screw clamping assembly 26. Because of the cross-sectional shape of the D-shaped extension 60, the base portion 34 of the bone screw clamping assembly 26 is able to slide on the D-shaped extension 60 of the rail member 50, though the base portion 34 is unable to rotate with respect to the D-shaped extension 60.

The rail member 50 further includes a groove 62 which is disposed on the surface of the D-shaped extension 60. The location of the groove 62 is such as to permit the groove 62 to be located adjacent to the aperture 44 when the D-shaped extension 60 of the rail member 50 is inserted into the D-shaped bore 52 of the base portion 34. As will be apparent to those skilled in the art, the threaded member 48 can then be inserted into the aperture 44 of the base portion 34 of the bone screw clamping assembly 26 so as to securely engage the groove 62 of the D-shaped extension 60 thereby preventing axial movement of the base portion 34 with respect to the rail member 50. In the preferred embodiment, the groove 62 includes graduated markings indicating the amount of longitudinal displacement of the bone screw clamping assembly 26 relative to the central body 24.

The central body 24 will now be described in greater detail with reference to FIGS. 5A, 5B, 6, 7, 8A, 8B and 9A–9C. The central body 24 includes a first and second connection members 70 and 72, respectively, as well as a first and second rotational components 75 and 76. The first and second connection members 70 and 72 serve to secure the central body 74 to the first and second bone screw clamping assemblies 26 and 28, respectively.

The first connection member 70 includes a female portion 80 which is able to be received within a bore 82 provided in a cylindrical end 84 of the rail member 50. The cylindrical end 84 includes an aperture 86 which is able to receive a threaded fastener 88. The threaded fastener engages a reduced diameter groove 90 formed in the female portion 80 of the first connection member 70 to secure the rail member 50 and the first connection member 70.

In a similar manner, the first rotational component 74 is attached to the second rotational component 76 and the second rotational 76 is attached to the second connection member 72. More particularly, the first rotational component 74 is formed to include a second aperture 104 having a hex-shaped recess 106 for receiving the base portion 96 of the washer 90. The second rotational component 76 includes a first aperture 108 which includes a hex-recess 110 and aligns with the aperture 104 of the first rotational component 74. The apertures 104 and 108 receive a threaded fastener 112 which defines a pivot axis therebetween. The aperture 104 is internally threaded for engaging the external threads of the fastener 112. Again similarly, the second rotational component 76 includes a second aperture 116 having a hex shaped recess 118. The second connection member 72 includes a recess 120 having a hex shaped recess 124 which aligns with the second aperture 116 of the second rotational component 76. The hex-shaped recesses 110 and 120 are adapted to receive the base 96 of a washer 90.

A plurality of grooved locking washers 90 are disposed between the first connection member 70 and the rotational component 74. In particular, the first rail connection member 70 has an aperture 92 with a hex-shaped recess 94 for receiving the base portion 96 of the washer 90. In a similar fashion, the first rotational component 72 includes an aperture 98 with a hex-shaped recess 100 for receiving the base portion 96 of the washer 90. Because the groove surface 102 of the washers 90 engage each other, the first connection member 70 is secured to the first rotational component 72 upon secured threaded engagement of a screw 104 with internal threads of the aperture 92. The screw 104 defines a pivot axis between the first connection member 70 and the first rotational component. The joint formed between the first connection member 70 and the first rotational component 72 permits approximately 60° of relative rotation. However, this range of relative rotation may be readily adjusted for particular applications.

Turning now to FIGS. 9(A)–(C), 10(A)–(B), and 11(A)–(B), and 12, the second bone screw clamping assembly 28 of the preferred embodiment of the apparatus 10 of the present invention will now be described in detail. The second bone screw clamping assembly 28 is shown to generally include a hinge assembly having a first hinge component 200 and a second hinge component member 202, a transverse member or bar assembly 204, and a pair of bone screw clamps or bar clamps 206 carried by the transverse member 204. The first hinge component 200 is generally U-shaped having two downwardly extending segments 208 and an arcuate segment 210 interconnecting the downwardly extending segments 208. The first hinge component 200 defines a radiographic window 212 for laterally viewing the anatomical hinge of the ankle joint 2.

As will be discussed below, the second bone screw clamping assembly is adjustable to receive the bone screws 16 after the bone screws 16 are inserted into the bones 5 and 6 of the foot 7. In the description that follows, reference will be made to relative movement of the bone screws 16. It will be understood that this relative movement is accomplished while the bone screws 16 are fixed with respect to the foot 7 through adjustment of the second bone screw clamping assembly 28.

To provide means for translating the bone screws 16a and 16b in a proximal/distal direction relative to the central body 24, the bar assembly 204 is movably engaged with the downwardly extending segments 208 of the first hinge component 200. The bar assembly 204 includes a hollow cylindrical sleeve 214 spanning between the downwardly extending segments 208 of the first hinge component 200. The ends 216 of the hollow cylindrical sleeve are enlarged and non-rotatably received in elongated slots 218 in an associated one of the downwardly extending segments 208. A threaded fastener 220 passes through the cylindrical sleeve 214. At a first end, the threaded fastener 220 includes a head 22 having a hex-recess 224 and a flange 225 slidably received within a recess 226 adjacent the slot 218. The other end of the threaded fastener 220 engages a captured nut 228 which is similarly formed to include a flange 230 received in a substantially identical recess 232. The captured nut 228 also includes a hex-recess 234. Upon rotation of either the head 232 or the captured nut 228, the bar assembly 204 can be fixed in a proximal/distal direction.

To provide means for translating the bone screws 16a and 16b in an anterior or posterior direction relative to the central body 24 and rotating the bone screws 16a and 16b about an axis defined by the cylindrical sleeve 204, the second bone screw clamping assembly 28 includes a pair of substantially identical bar clamps 206. The bar clamps 206 (specifically shown in FIGS. 11A and 12) are each shown to include a first portion 240 for engaging the cylindrical sleeve 214 and a second portion 242 for clamping one of the bone screws 16 which are interconnected by a threaded fastener 244. The first portion 240 defines a recess 246 for receiving the cylindrical sleeve 204 and includes upper and lower flanges 248 and 250 spaced apart by a gap 252. The upper and lower flanges 248 and 250 include aligning apertures 254 for receiving the fastener 244. The second portion 242 is similarly formed to define an aperture 256 for receiving one of the bone screws 16 and includes upper and lower flanges 258 and 260 having aligning apertures 262 for receiving the threaded fastener 244. The aperture 262 of the lower portion 260 is internally threaded. Cooperating locking surfaces 264 are provided on adjacent surfaces of the first and second portions 240 and 242.

When the threaded fastener 244 passing through the aligning apertures 254 and 262 of the first and second portions 240 and 242 and is initially tightened, the first and second portions 240 and 242 are drawn together preventing rotation of the second portion 242 relative to the first portion 240 due to the cooperating locking surfaces 264. Further tightening of the threaded fastener 244 functions to clamp one of the bone screws 16 within the aperture 256 and clamp the cylindrical sleeve 214 within the aperture 246.

It will be appreciated that the bar clamps 206 allow adjustment of the bone screw pivot axis relative to the bone screws 16 in various distinct anatomical directions. In this regard, initial loosening of the threaded fastener 244 allows the associated clamp 206 to be everted/inverted or translated in the anterior/posterior direction. Further loosening of the fastener 244 allows the associated clamp 206 to be internally/externally rotated. Loosening of the fastener 220 allows for proximal/distal translation of the bar assembly 204 and thus the clamps 206.

The second hinge component 202 is interconnected to the central body 24 through a female portion 270 which is received within a cylindrical aperture 272 defined by the second connection member 72. The female portion 270 includes a reduced diameter portion 274 adapted to align with an aperture 276 which intersects the cylindrical recess 272. The aperture 276 receives a locking screw (not shown) which engages the reduced diameter portion 274 and retains the female portion 270 within the cylindrical aperture 272. In the preferred embodiment, the female portion 270 is carried by a flange 278 on its opposite side, the flange 278 includes a male extension (not shown) which is received into a female recess (not shown) formed in a body 284 of the second hinge member 202. A pin (not shown) secures the male extension to the body 284.

To provides means for articulating the first hinge portion 200 relative to the second hinge portion 202, the apparatus 10 of the present invention is shown to include a generally rectangular recess 288 which passes through the body 284 of the second hinge portion 202 and slidably receives the arcuate segment 210 of the first hinge portion 200. A threaded aperture 290 passes through a side of the body 284 of the second hinge portion 202 and intersects the rectangular aperture 288. The aperture 290 receives a locking screw 292 adapted to engage a groove 294 formed in the arcuate segment 210 of the first hinge portion 200 for securing the relative position of the first hinge portion 200 relative to the second hinge portion 202. In the preferred embodiment, a plastic insert 280 is interdisposed between the male extension carried by the flange 278 and the aperture 288 to effectively provide a bearing surface against which the arcuate segment 210 of the first hinge portion 220 may slide when articulated relative to the second hinge portion 202.

The first and second hinge portions 200 and 202 of the second clamping member 228 function as a floating hinge pivotally interconnecting the bone screws 16 with the central body 24 and in turn the bone screws 14. The axis about which the bone pins 16 rotate relative to the central body when the first and second hinge portions 200 and 202 are articulated is defined by the center of curvature for the arcuate segment 210 of the first hinge portion 200. Significant to the present invention, this bone screw pivot axis is located within the radiographic window 212 which is defined by the second clamping assembly 28. As a result, the anatomical pivot axis of the ankle joints 2 may be aligned with the pivot axis for the screws 16, thereby permitting radiographic access to the anatomical ankle joint 2 in a lateral direction.

With reference to FIG. 13, an alternative construction for a second bone screw clamping assembly 28' is illustrated. In this embodiment, similar reference numerals will be used to identify similar components as previously described with respect to the preferred embodiment of the present invention. As with the first preferred embodiment of the present invention, the second clamping assembly 28' includes first and second components 200 and 202 adapted to move relative to one another for pivoting a pair of bone screws (not shown with respect to FIG. 13) about an axis. The first and second components 200 and 202 are shown interconnected through a worm gear 300 having a threaded fastener 302 with a plurality of external teeth 304 operatively engaged with a plurality of grooves 306 formed in an arcuate segment 210 of the first component 200. The arcuate segment 210 again has a center of curvature which defines the pivot axis for the bone screws. The worm gear 300 allows for rotation to be restricted to a predefined range of motion and further allows for application of motorized motion under force or displacement control.

As with the first embodiment, the first component 200 of the second clamping assembly 28' defines a radiographic window 212 for providing radiographic access to the ankle joint from a lateral view. The alternative embodiment 28' further includes a radiographic member 310 for aligning the bone screw pivot axis with the anatomical pivot axis of the ankle joint 2. In the exemplary embodiment illustrated, the radiographic member 310 is generally L-shaped and has a pair of legs 312 removably attached to the second component 200 with studs 314 adapted to engage apertures (not shown) in the arcuate segment 210. A target 316 is identified at the intersection of the legs 312 which is adapted to be centered on the radius of curvature of the arcuate segment 210 and thereby on the bone screw pivot axis. The radiographic member 310 is preferably constructed of a radiolucent material such as plexiglass or the like. Only the target 316 is intended to appear radiographically. In use, the radiographic member 310 assists in precisely aligning the anatomical pivot axis of the ankle joint with the bone screw pivot axis identified with the target 316.

In this alternative embodiment, the bone screws 16a and 16b are each captured in a bronze bearing 318 provided within the aperture 256. The bearing 318 allows for rotation of the associated bone screws 16 within the bar clamp 206 about their longitudinal axes. As a result, the clamps 206 hold the apparatus 10 in place, but the bone screws 16 can rotate within the clamp 206. Therefore, no torque results at the bone screwbone interface. In this regard, if the bone screws 16 are rigidly held in place, the calcaneus 6 can experience a moment around the bone screw 16b due to impingement in the ankle joint 2 or due to forces to the heel. This moment can initiate small rotations of the calcaneus 6 around the bone screws 16b followed by successive loosening of the bone screws 16b. This problem is effectively eliminated by the bronze bearings 318.

According to the above description, the apparatus 10 of the present invention provides a hinge joint which can be locked or unlocked. It is anticipated that the apparatus 10 can be used in at least the following distinct application modes:

1. As a locked hinge typically for a short post-operative period.
2. As a unlocked hinge for examination by a surgeon.
3. For active motion in a restricted range of motion.
4. For passive motion (e.g., motorized) in a restrictive range of motion (displacement control).
5. For passive motion (e.g., motorized) under force control. The application mode for restrictive range of motion (#3) is useful for avoiding excessive joint forces at the extremes of physiologic motion that may result. The use of motorized motion under force control (#4) can be used to overcome any introduction of impingement problems at the end stops of each motion cycle. The application modes identified as 4 and 5 above can be used to monitor the number of performed motion cycles and to assess changes in range of motion for an applied moment.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for external fixation of a hinged joint having an anatomical pivot axis with first and second skeletal elements on opposite sides of the anatomical pivot axis, the apparatus comprising:

a first bone screw adapted to be connected to the first skeletal element;

a second bone screw adapted to be connected to the second skeletal element;

means for receiving said first bone screw;

means for receiving said second bone screw, said means for receiving said second bone screw being operative to at least partially define a radiographic window permitting radiographic examination of the anatomical pivot axis;

means for securing said means for receiving said first bone screw to said means for receiving said second bone screw; and means for articulating said second bone screw about a pivot axis passing through said radiographic window including a first hinge component having an arcuate segment, said arcuate segment having a center of curvature which defines said pivot axis, said first hinge component being generally U-shaped including a pair of legs downwardly extending from said arcuate segment, and further comprising a transverse member interconnecting said pair of legs and a clamping member for receiving the second bone screw attached to said transverse member, said clamping member being translatable along said transverse member.

2. The apparatus for external fixation of a joint of claim 1, wherein said means for articulating said second bone screw about a pivot axis passing through said radiographic window further includes a second hinge component including a recess for slidably receiving said first hinge component.

3. The apparatus for external fixation of a joint of claim 1, wherein said means for receiving said second bone screw includes bearing means for permitting rotation of said second bone screw about its longitudinal axis.

4. The apparatus for external fixation of a joint of claim 3, wherein said transverse member is adjustable in an anterior/posterior direction along said pair of legs.

5. An apparatus for external fixation of an ankle joint having an anatomical pivot axis interdisposed between first and second skeletal elements, the first skeletal element located on the distal side of the ankle joint, the apparatus comprising:

a bone screw adapted to be connected to the first skeletal element; and a clamping assembly including a bone screw clamp for receiving the bone screw and at least partially defining a radiographic window permitting lateral radiographic examination of the anatomical pivot axis, said clamping assembly further including a hinge assembly defining a bone screw pivot axis about which said bone screw may selectively rotate, said bone screw pivot axis adapted to substantially align with the anatomical pivot axis, said clamping assembly including first and second hinge components for articulating said bone screw about said bone screw pivot axis passing through said radiographic window, said first hinge component including an arcuate segment having a center of curvature defining said bone screw pivot axis, said second hinge component including a recess for slidably receiving said first hinge component, said first hinge component being generally U-shaped including a pair of legs downwardly extending from said arcuate segment.

6. The apparatus for external fixation of an ankle of claim 5, further comprising a transverse member interconnecting said pair of legs, said screw clamp being movably attached to said transverse member, said transverse member is adjustable in an anterior/posterior direction along said pair of legs.

7. The apparatus for external fixation of an ankle of claim 6, further comprising a bearing interdisposed between said bone screw and said bone screw clamp, said bearing permitting rotation of said bone screw about its longitudinal axis.

8. An apparatus for external fixation of an ankle joint, the ankle joint having an anatomical pivot axis located between the tibia on one side and talus and calcaneus on the other side, the apparatus comprising:

a first bone screw adapted to be connected to the talus;

a second bone screw adapted to be connected to the calcaneus;

a clamping assembly including first and second bone screw clamps for receiving said first and second bone screws, respectively;

said clamping assembly further including a hinge assembly defining a bone screw pivot axis about which said first and second bone screws may selectively rotate, said bone screw pivot axis adapted to substantially align with the anatomical pivot axis;

said first and second bone screw clamps being linearly adjustable in an anterior/posterior direction relative to said bone screw pivot axis;

whereby said first and second bone screw clamps can be adjusted relative to the bone screw pivot axis after said first and second bone screws are connected to the talus and calcaneus, respectively, for purposes of precisely aligning said bone screw pivot axis and said anatomical pivot axis;

said hinge assembly comprising a first hinge component including a generally arcuate segment having a center of curvature which defines said bone screw pivot axis, said first hinge component including a pair of legs downwardly extending from said arcuate segment;

said clamping assembly further including a transverse member interconnecting said pair of legs, said first and second bone screw clamps being movably attached to said transverse member.

9. The apparatus for external fixation of an ankle of claim 8, wherein said first and second bone screw clamps are adjustable in a proximal/distal direction relative to said bone screw pivot axis.

10. An apparatus for external fixation of an ankle of claim 8, wherein said first hinge component at least partially defines a radiographic window so as to permit lateral radiographic examination of the anatomical pivot axis, said center of curvature being located within said radiographic window.

11. An apparatus for external fixation of a joint, the joint having an anatomical pivot axis located between a first bone and a second bone the apparatus comprising:

a first bone screw adapted to be connected to the first bone;

a second bone screw adapted to be connected to the second bone;

a first clamping assembly including a bone screw clamp for receiving said first bone screw;

a second clamping assembly including a bone screw clamp for receiving said second bone screw, said second clamping assembly including a hinge assembly defining a bone screw pivot axis about which said second bone screw may selectively rotate, said hinge assembly comprising a first hinge component and a second hinge component, said first hinge component including a generally arcuate segment having a center of curvature which defines said bone screw pivot axis, said first hinge component including a pair of legs downwardly extending from said arcuate segment, said clamping assembly further including a transverse member interconnecting said pair of legs, said bone screw clamps of said second clamping assembly attached to said transverse member; and a central body interconnecting said first and second clamping assemblies.

12. An apparatus for external fixation of a joint of claim 11, wherein said bone screw clamp of said second clamping assembly is movably attached to said transverse member.

13. An apparatus for external fixation of a joint of claim 11, wherein said first hinge component includes a recess for slidably receiving said first hinge component.

14. An apparatus for external fixation of a joint of claim 11, wherein said bone clamp of said second clamping assembly is mounted for rotation about said transverse member.

15. An apparatus for external fixation of a joint of claim 11, wherein said second clamping assembly defines a radiographic window permitting radiographic examination of the anatomical pivot axis.

16. An apparatus for external fixation of a joint of claim 15, wherein said bone screw pivot axis passes through said radiographic window.

17. An apparatus for external fixation of a joint of claim 11, wherein said bone screw pivot axis is adapted to substantially align with the anatomical pivot axis.

* * * * *